United States Patent [19]

Wright et al.

[11] Patent Number: 4,505,907

[45] Date of Patent: Mar. 19, 1985

[54] N-FORMYL AND N-HYDROXYMETHYL-3-PHENOXY-1-AZETIDINECARBOXAMIDES

[75] Inventors: George J. Wright, Midlothian; Lina C. Teng, Richmond, both of Va.

[73] Assignee: A. H. Robins Company, Inc., Richmond, Va.

[21] Appl. No.: 414,101

[22] Filed: Sep. 2, 1982

[51] Int. Cl.³ .................. A61K 31/395; C07D 205/04
[52] U.S. Cl. ................................. 514/210; 260/239 A
[58] Field of Search ................ 260/239 AR; 424/244

[56] References Cited

U.S. PATENT DOCUMENTS 3,823,006  7/1974  Lorenz et al. ............... 260/239 AR
4,031,221  6/1977  Helsley et al. .............. 260/239 AR
4,226,861 10/1981  Cale, Jr. ..................... 260/239 AR
4,379,151  4/1983  Cale, Jr. ..................... 260/239 AR

OTHER PUBLICATIONS

March, ed., *Advanced Organic Chemistry*, 2nd ed., pp. 382–385, (1977), New York McGraw–Hill.

Primary Examiner—Donald G. Daus
Assistant Examiner—William A. Teoli, Jr.

[57]  ABSTRACT

N-Formyl and N-hydroxymethyl-3-phenoxy-1-azetidinecarboxamides having the formula:

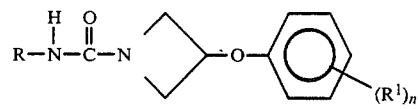

wherein R is selected from formyl and hydroxymethyl and $R^1$ is selected from hydrogen, fluoro, loweralkyl, loweralkoxy, trifluoromethyl, acetyl, N-formylcarboxamido or N-hydroxymethylcarboxamido having antidepressant activity are disclosed.

3 Claims, No Drawings

N-FORMYL AND N-HYDROXYMETHYL-3-PHENOXY-1-AZETIDINECARBOXAMIDES

BACKGROUND OF THE INVENTION

1. Field of Invention

The present invention relates to novel N-formyl and N-hydroxymethyl-3-phenoxy-1-azetidinecarboxamides which exhibit anticonvulsant activity in animals and are effective in treatment of epilepsy in humans.

2. Description of the Prior Art

N-Loweralkyl-3-phenoxy-1-azetidinecarboxamides are disclosed in U.S. Pat. No. 4,226,861 as having anticonvulsant activity and useful in the treatment of epilepsy.

Unsubstituted-3-phenoxy-1-azetidinecarboxamides are the subject of copending U.S. application Ser. No. 409,476 filed Aug. 19, 1982, which compounds have longer lasting anticonvulsant effect and anti-epilepsy utility absent muscle relaxant side effects at effective anticonvulsant doses.

Certain of the compounds of the present invention were discovered as metabolites in the blood-stream of animals treated with the above-mentioned N-methyl analogs and have greater longevity in the blood-stream and greater persistence in their anticonvulsant effect.

OBJECTS AND SUMMARY OF THE INVENTION

The compounds of the present invention have the formula:

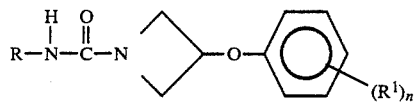

wherein;

R is selected from formyl or hydroxymethyl;

$R^1$ is selected from the group consisting of hydrogen, fluoro, loweralkyl, loweralkoxy, trifluoromethyl, acetyl, N-formylcarboxamido or N-hydroxymethylcarboxamido;

n is selected from 1 to 3 inclusive wherein $R^1$ may be the same or different.

In the further definition of symbols in Formula I and where they appear elsewhere throughout this specification and in the claims the terms have the following significance.

The term "loweralkyl" includes straight and branched chain hydrocarbon radicals of up to eight carbon atoms inclusive and is exemplified by such groups as methyl, ethyl, propyl, isopropyl, butyl, isobutyl, tertiary-butyl, amyl, isoamyl, hexyl, heptyl, octyl, and the like.

The term "loweralkoxy" has the formula O-loweralkyl.

The compounds of Formula I are useful because of their pharmacological action on the central nervous system.

The procedure for establishing anticonvulsant activity of the compounds of this invention and comparison with prior art compounds is based on evaluation techniques using metrazol as convulsant published by Swinyard, E. A. in EPILEPSIA 10: 107-19 (1969) and in J. PHARMAC. EXPTL. THERAP. 106: 319-30 (1952) as described in greater detail hereinbelow.

Sequence of reaction in preparation of compounds of Formula I is diagrammed in Chart I. The preparation of certain of the compounds of Formula III is also disclosed in copending U.S. application Ser. No. 312,046 filed Oct. 16, 1981, and the preparation of the compounds of Formula II is also disclosed in U.S. application Ser. No. 409,476, filed Aug. 19, 1982. Compounds of Formula IV wherein $R^2$ is α-methylbenzyl or diphenylmethyl are prepared by reacting compounds of Formula V and VI at temperatures up to about 80°–100° C. for periods of 2 to 5 hours in dimethylformamide. Compounds of Formula III are prepared by hydrogenolysis of compounds of Formula IV, usually in the presence of a lower-alkanol solvent, ethanol being preferred. The rate of hydrogenolysis is dependent somewhat on time and temperature, a higher temperature generally decreasing the time required for complete hydrogenolysis. Typical times vary from about 3 hr to about 24 hr at temperatures of 50°–90° C.

Compounds of Formula II are prepared by reacting compounds of Formula III with nitrogen in solution, conveniently for example in a mixture of ethanol and methylene chloride or acetone at room temperature usually until analysis indicates substantial reaction has occurred and isolating by evaporation of reaction solvent, partitioning with water and an organic solvent for the compound, separating and evaporating the organic solvent layer and recrystallizing.

Compounds of Formula I wherein R is formyl are prepared by reacting compounds of Formula II with formic acid such as the free acid or its salts, acetic-formic anhydride or methyl and ethyl orthoformate, preferably acetic-formic anhydride. Conveniently, a solvent such as methylene chloride is employed in the reaction mixture. When acetic-formic anhydride is the source of formic acid, temperatures of 10° to 60° C. for the reaction are appropriate, preferably 20°-30° C. and the product may be isolated by evaporating, partitioning the residue in a solvent such as methylene chloride and water, separating, drying and evaporating the solvent layer to dryness, triturating the residue with ether, filtering and drying as in Example 1.

Compounds of Formula I wherein R is hydroxymethyl are prepared by reacting compounds of Formula II with warm formaldehyde solution, preferably at about 60°-70° C. The product is extracted with a solvent such as ether and worked up for purification as in Example 4.

Preparations 1-18 illustrate the preparation of compounds of Formula III and their precursors and Preparations 19-21 illustrate the preparation of compounds of Formula II. The examples illustrate the conversion of 3-phenoxy-1-azetidinecarboxamides to their N-formyl and N-hydroxymethyl derivatives (Formula I). It will be apparent to those skilled in the art that modifications may be practiced without departing from the purpose and intent of the disclosure.

CHART I

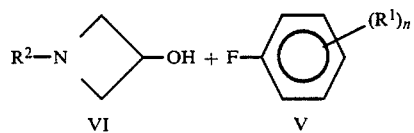

-continued
CHART I

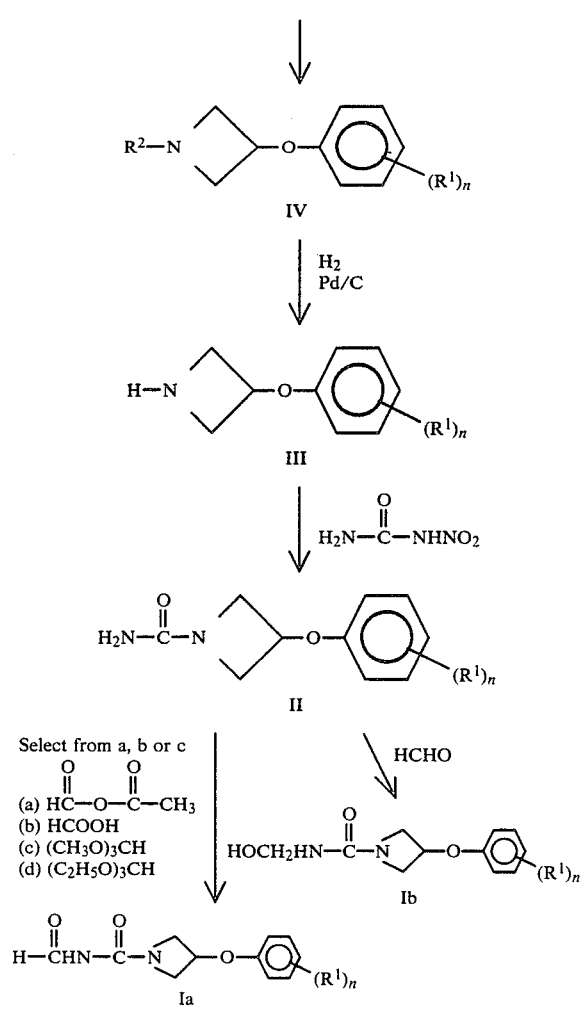

PREPARATION 1

3-(3-Chlorophenoxy)-1-(α-methylbenzyl)azetidine Oxalate 1-(α-Methylbenzyl)-3-hydroxyazetidine maleate (393 g., 1.3 moles) was partitioned in dilute potassium hydroxidebenzene. The separated dried benzene solution was concentrated, the residual oil dissolved in 250 ml. of dimethylformamide and added dropwise to a stirred suspension of 53 g. (1.1 moles) of 50% sodium hydride in 750 ml. of dimethylformamide at 90° C. The mixture was heated at 90° C. for 1 hr. and 130.5 g. (1 mole) of 3-chlorofluorobenzene added dropwise at 90° C. The mixture was refluxed for 3 hrs., cooled and partitioned between isopropyl ether and dilute sodium hydroxide. The isopropyl ether solution was dried, concentrated, and the residue added to 1200 ml. of isopropyl alcohol containing 90 g. (1 mole) of oxalic acid. The oxalate salt was recrystallized from ethanol. Yield 263 g. (69%); m.p. 141°–144° C.

Analysis: Calculated for $C_{19}H_{20}ClNO_5$: C,60.40; H,5.34; N,3.71. Found: C,60.19; H,5.55; N,3.60.

PREPARATION 2

1-(α-Methylbenzyl)-3-(4-trifluoromethylphenoxy)azetidine

The maleate salt of 1-(α-methylbenzyl)-3-hydroxyazetidine (78.6 g., 0.20 mole) was partitioned between benzene and dilute sodium hydroxide, the benzene layer dried, filtered, and concentrated at reduced pressure. The residue was dissolved in 100 ml. of dry dimethylformamide and added at a rapid dropwise rate, to a stirring suspension of 10.1 g. (0.22 mole) of sodium hydride (50% in mineral oil) in 150 ml. of dry dimethylformamide at 90° C. The solution was heated at 90° C. for one hour and then treated dropwise with 32.0 g. (0.20 mole) of 4-trifluoromethylfluorobenzene. The solution was refluxed for three hours. The cooled solution was partitioned between water and isopropyl ether, and the ether layer extracted with dilute hydrochloric acid. The aqueous acid layer was made basic with concentrated sodium hydroxide and ice, and extracted with isopropyl ether. The ether layer was concentrated and the residue distilled at 150°–160° C./0.2 mm. to give 25.6 g of product.

Analysis: Calculated for $C_{18}H_{18}F_3NO$: C,67.28; H,5.65; N,4.36. Found: C,67.27; H,5.84; N,4.34.

Preparations 3 to 7 were prepared according to the procedures set forth in detail in Preparations 1 and 2 by reacting 1-(α-methylbenzyl)-3-azetidinol with the appropriately substituted fluorobenzene. The physical constants are shown in Table I.

TABLE I

| Preparation | R | M.P. (b.p.) °C. | Salt |
|---|---|---|---|
| 3 | 2-CONH$_2$ | 148–52 | — |
| 4 | 4-CN | 65–8 | — |
| 5 | 3-CF$_3$ | 150–3 | (COOH)$_2$ |
| 6 | 2-CF$_3$ | 162–3 | (COOH)$_2$ |
| 7 | 3-CN | [1](185–90) | — |

[1]At 0.2 mm.

The analytical data of Preparations 3 to 7 are shown in Table II.

TABLE II

Analytical Data on Preparations 3 to 7

| Preparation | Empirical Formula | Calculated | | | Found | | |
|---|---|---|---|---|---|---|---|
| | | C | H | N | C | H | N |
| 3 | $C_{18}H_{20}N_2O_2$ | 72.95 | 6.80 | 9.45 | 72.56 | 6.78 | 9.32 |
| 4 | $C_{18}H_{18}N_2O$ | 77.67 | 6.52 | 10.06 | 77.61 | 6.53 | 10.01 |
| 5 | $C_{20}H_{20}F_3NO_5$ | 58.39 | 4.90 | 3.41 | 57.99 | 4.97 | 3.39 |
| 6 | $C_{20}H_{20}F_3NO_5$ | 58.39 | 4.90 | 3.41 | 58.15 | 4.89 | 3.37 |
| 7 | $C_{18}H_{18}N_2O$ | 77.67 | 6.52 | 10.06 | 77.32 | 6.54 | 9.87 |

PREPARATION 8

3-[1-(α-Methylbenzyl)-3-azetidinyloxy]benzamide Oxalate

3-[1-(α-Methylbenzyl)-3-azetidinyloxy]benzonitrile (50.0 g., 0.18 mole) in 500 ml of t-butyl alcohol was treated with 50.0 g. of finely ground potassium hydroxide. The mixture was stirred at reflux for 30 min. Ice and water were added to the reaction mixture and the organic layer was separated and dried over sodium sulfate. The dried filtered solution was concentrated at reduced pressure. The residue was dissolved in methanol and treated with an equivalent of oxalic acid, and the oxalate salt was recrystallized from ethanol to give 11.4 g. (16%) of product, (m.p. 145° C.).

Analysis: Calculated for $C_{20}H_{22}N_2O_6$: C,62.17; H,5.74; N,7.25. Found: C,62.17; H,5.80; N,7.20.

PREPARATION 9

4-[1-(α-Methylbenzyl)-3-azetidinyloxy]benzamide

To 45.0 g. (0.16 mole) of 4-[1-(α-methylbenzyl)-3-azetidinyloxy]benzonitrile in 500 ml of t-butyl alcohol was added 45.0 g. of finely ground potassium hydroxide. The mixture was stirred and refluxed for 30 minutes. Ice and water were added and a thick white solid separated. The solid was recrystallized from toluene to give 30.0 g. (63%) of product melting at 174°–178° C.

Analysis: Calculated for $C_{18}H_{20}N_2O_2$: C,72.05; H,6.80; N,9.45. Found: C,73.06; H,6.79; N,9.44.

PREPARATION 10

1-Diphenylmethyl-3-phenoxyazetidine

To a stirred suspension of 8.6 g. (0.22 mole) of sodium amide in 100 ml. of dry toluene was added 18.2 g. (0.2 mole) of phenol in 50 ml. of dry toluene. After stirring for 2 hrs. at 60° C. the pot temperature was raised to 80° C. and a solution of 1-diphenylmethyl-3-methylsulfonyloxyazetidine (63.4 g., 0.2 mole) in 200 ml. of dry toluene was added dropwise. After an additional 2 hrs. at 80° C. the cooled mixture was treated with water, the toluene layer was extracted with dilute sodium hydroxide solution, dried and concentrated at reduced pressure. The residue was crystallized twice from a water-isopropanol mixture. The free base melted at 83°–85° C.

Analysis: Calculated for $C_{22}H_{21}NO$: C,83.78; H,6.71; N,4.44. Found: C,83.69; H,6.81; N,4.41.

PREPARATION 11

3-(Phenoxy)azetidine Methanesulfonate

A 200 ml. solution of 7.8 g (0.025 mole) of 1-diphenylmethyl-3-phenoxyazetidine in ethanol was treated with 20% Pd(OH)$_2$ on carbon and hydrogenated for 23 hrs. at about 45 psi and 80° C. The mixture was filtered and the filtrate concentrated. The residue was diluted to 30 ml. with ethanol and 2.5 g. of methanesulfonic acid added. The isolated methanesulfonate salt was recrystallized from ethanol. The salt weighed 2.3 g. (37.5%) and melted at 128°–130° C.

Analysis: Calculated for $C_{10}H_{15}NO_4S$: C,48.97; H,6.16; N,5.71. Found: C,48.40; H,6.19; N,5.63.

The compound was also prepared by hydrogenolysis of 1-(α-methylbenzyl)-3-(3-chlorophenoxy)azetidine in isopropyl alcohol using the same type catalyst and conditions.

PREPARATION 12

3-[4-(Trifluoromethyl)phenoxy]azetidine Oxalate

To 24.0 g. (0.075 mole) of 3-[4-(trifluoromethyl)-phenoxy]-1-(α-methylbenzyl)azetidine in 150 ml. of ethanol was added 0.5 g. of 20% Pd(OH)$_2$ on carbon, and the mixture was hydrogenated for five hours at 80° C. and 45 psi. The mixture was cooled, filtered, and the filtrate concentrated at reduced pressure. The residue was dissolved in ethanol and treated with oxalic acid, and the oxalate salt was recrystallized three times in ethanol. The yield was 3.0 g. (13%) and the salt melted at 176°–178° C.

Analysis: Calculated for $C_{12}H_{12}F_3NO_3$: C,46.91; H,3.94; N,4.56. Found: C,47.07; H,3.96; N,4.59.

The compounds in Preparations 13 to 17 are prepared according to the procedure set forth in detail in Preparations 11 and 12 by hydrogenolysis of the α-methylbenzyl radical attached to the azetidine nitrogen. The physical constants are shown in Table 1.

TABLE 1

$$H-N\underset{}{\diamondsuit}-O-\underset{}{\diamondsuit}-R$$

| Preparation | R | M.P. °C. | Salt |
|---|---|---|---|
| 13 | 2-CONH$_2$ | 173–75 | CH$_3$SO$_3$H |
| 14 | 3-CF$_3$ | 123–25 | [1]C$_6$H$_{11}$NHSO$_3$H |
| 15 | 2-CF$_3$ | 154–56 | HCl |
| 16 | 3-CONH$_2$ | 160–63 | — |
| 17 | 4-CONH$_2$ | 187–88 | (COOH)$_2$ |

[1]N—cyclohexylsulfamate.

The analytical data of Preparations 13 to 17 are shown in Table 2.

TABLE 2

Analytical Data on Preparations 13 to 17

| Preparation | Empirical Formula | Calculated C | H | N | Found C | H | N |
|---|---|---|---|---|---|---|---|
| 13 | C$_{11}$H$_{16}$N$_2$O$_5$S | 45.42 | 5.59 | 9.72 | 45.48 | 5.65 | 9.45 |
| 14 | C$_{16}$H$_{23}$F$_3$N$_2$O$_4$S | 48.48 | 5.85 | 7.07 | 48.08 | 5.94 | 6.97 |
| 15 | C$_{10}$H$_{11}$ClF$_3$NO | 47.35 | 4.37 | 5.52 | 47.12 | 4.32 | 5.45 |
| 16 | C$_{10}$H$_{12}$N$_2$O$_2$ | 62.49 | 6.29 | 14.57 | 62.06 | 6.13 | 13.98 |
| 17 | C$_{12}$H$_{14}$N$_2$O$_6$ | 51.07 | 5.00 | 9.93 | 51.39 | 5.22 | 9.56 |

PREPARATION 18

When in the procedure of Preparation 12 the following are substituted for 3-[4-(trifluoromethyl)phenoxy]-1-(α-methylbenzyl)azetidine:

3-[4-(methyl)phenoxy]-1-(α-methylbenzyl)azetidine,
3-[4-(methoxy)phenoxy]-1-(α-methylbenzyl)azetidine,
3-[3,5-(dimethoxy)phenoxy]-1-(α-methylbenzyl)azetidine,
3-[3-(fluoro)phenoxy]-1-(α-methylbenzyl)azetidine, and
3-[4-(acetyl)phenoxy]-1-(α-methylbenzyl)acetidine,
there are obtained:
3-[4-(methyl)phenoxy]azetidine oxalate,
3-[4-(methoxy)phenoxy]azetidine oxalate,
3-[3,5-(dimethoxy)phenoxy]azetidine oxalate,
3-[3-(fluoro)phenoxy]azetidine oxalate, and
3-[4-(acetyl)phenoxy]azetidine oxalate.

PREPARATION 19

3-[3-(Trifluoromethyl)phenoxy]-1-azetidinecarboxamide

To a solution of 2.2 g (0.01 mole) of 3-[3-(trifluoromethyl)phenoxy]azetidine in 45 ml of methylene chloride and 45 ml of absolute ethyl alcohol was added 7 g (0.066 mole) of nitrourea and the mixture was stirred at room temperature for 48 hr. The mixture was filtered. The filtrate was evaporated to dryness and the residue was partitioned between 75 ml methylene chloride and 75 ml water. The water layer was extracted three times with 50 ml of methylene chloride. The methylene chloride extracts were combined and evaporated to dryness.

The residue was treated (washed) with a mixture of 1 ml methylene chloride and 20 ml of toluene and filtered. The precipitate was recrystallized from ethanol-water to give pale yellow crystals. The crystals were mixed with 2 ml of methylene chloride and 20 ml toluene and the mixture was heated on a steam bath for 2 hrs. The mixture was stored in a refrigerator for approximately 72 hrs. and filtered to give 1.2 g of the product as white crystalline needles, m.p. 151°–152° C.

Analysis: Calculated for $C_{11}H_{11}N_2O_2F_3$: C,50.77; H,4.26; N,10.77. Found: C,50.72; H,4.25; N,10.74.

PREPARATION 20

3-[3-(Trifluoromethyl)phenoxy]-1-azetidinecarboxamide

A mixture of 30.6 g (0.141 mole) of 3-[3-trifluoromethyl)phenoxy]azetidine and 42 g (0.321 mole) of nitrourea (80%) in 500 ml of acetone was stirred for 5 days (5 days not required, but convenient) at room temperature. The mixture was filtered and the filtrate concentrated in vacuo. The residue was partitioned between 150 ml of water and 100 ml of ethyl acetate and the layers separated. The aqueous layer was washed with 100 ml of ethyl acetate. The ethyl acetate layers were washed with 75 ml of 5% aqueous sodium hydroxide solution followed by 75 ml of water, dried over sodium sulfate and concentrated in vacuo. The residual oil was crystallized from ethyl alcohol-ethyl acetate to give 22 g (60%) substantially the title compound. Recrystallization twice from ethyl alcohol gave 9.9 g of white crystalline solid, m.p. 151°–152.5° C.

Analysis: Calculated for $C_{11}H_{11}N_2O_2F_3$: C,50.77; H,4.26; N,10.76. Found: C,50.90; H,4.29; N,10.71.

PREPARATION 21

When in the procedure of Preparation 20 the following are substituted for 3-[3-(trifluoromethyl)phenoxy]azetidine:
3-(phenoxy)azetidine,
3-[4-(trifluoromethyl)phenoxy]azetidine,
3-[2-(trifluoromethyl)phenoxy]azetidine,
3-[4-(methyl)phenoxy]azetidine,
3-[4-(methoxy)phenoxy]azetidine,
3-[3,5-(dimethoxy)phenoxy]azetidine,
3-[3-(fluoro)phenoxy)]azetidine,
2-(3-azetidinyloxy)benzamide,
3-(3-azetidinyloxy)benzamide,
4-(3-azetidinyloxy)benzamide, and
3-[4-(acetyl)phenoxy]azetidine,
there are obtained:
3-(phenoxy)-1-azetidinecarboxamide,
3-[4-(trifluoromethyl)phenoxy]-1-azetidinecarboxamide,
3-[2-(trifluoromethyl)phenoxy]-1-azetidinecarboxamide,
3-[4-(methyl)phenoxy]-1-azetidinecarboxamide,
3-[3,5-(dimethoxy)phenoxy]-1-azetidinecarboxamide,
3-[3-(fluoro)phenoxy]-1-azetidinecarboxamide,
3-[2-(carboxamido)phenoxy]-1-azetidinecarboxamide,
3-[3-(carboxamido)phenoxy]-1-azetidinecarboxamide,
3-[4-(carboxamido)phenoxy]-1-azetidinecarboxamide, and
3-[4-(aceto)phenoxy]-1-azetidinecarboxamide.

EXAMPLE 1

N-Formyl-3-[3-(trifluoromethyl)phenoxy]-1-azetidinecarboxamide

A mixture of 0.524 g (0.002 mole) of 3-[3-(trifluoromethyl)phenoxy]-1-azetidinecarboxamide and 1.5 ml of formic acetic anhydride (prepared by reacting sodium formate and acetyl chloride in ether at 23°–27° C. for 5.5 hr, filtering and evaporating off the ether) was stirred at room temperature for about 54 hr. The mixture was evaporated to dryness and the residue was partitioned between 7 ml methylene chloride and 2 ml water. The methylene chloride layer was separated, dried over sodium sulfate and evaporated to dryness. The residue was triturated with ether and the mixture subjected to filtration to give a solid white filter cake weighing 0.398 g after drying. The solid was stirred with more ether for 10 minutes and the mixture filtered to give 0.350 g (61%) white powder, m.p. 117.5°–119° C.

Analysis: Calculated for $C_{12}H_{11}N_2O_3F_3$: C,50.00; H,3.84; N,9.72. Found: C,49.94; H,3.85; N,9.68.

EXAMPLE 2

When in the procedure of Example 1, the following are substituted for 3-[3-(trifluoromethyl)phenoxy]-1-azetidinecarboxamide:
3-(phenoxy)azetidinecarboxamide,
3-[4-(trifluoromethyl)phenoxy]-1-azetidinecarboxamide,
3-[2-(trifluoromethyl)phenoxy]-1-azetidinecarboxamide,
3-[4-(methyl)phenoxy]-1-azetidinecaboxamide,
3-[3,5-(dimethoxy)phenoxy]-1-azetidinecarboxamide,
3-[3-(fluoro)phenoxy]-1-azetidinecarboxamide, and
3-[4-(aceto)phenoxy]-1-azetidinecarboxamide,
there are obtained:
N-formyl-3-(phenoxy)azetidinecarboxamide,
N-formyl-3-[4-(trifluoromethyl)phenoxy]-1-azetidinecarboxamide,
N-formyl-3-[2-(trifluoromethyl)phenoxy]-1-azetidinecarboxamide,
N-formyl-3-[4-(methyl)phenoxy]-1-azetidinecarboxamide,
N-formyl-3-[3,5-(dimethoxy)phenoxy]-1-azetidinecarboxamide,
N-formyl-3-[3-(fluoro)phenoxy]-1-azetidinecarboxamide, and
N-formyl-3-[4-(aceto)phenoxy]-1-azetidinecarboxamide.

EXAMPLE 3

When in the procedure of Example 1, the following are substituted for 3-[3-(trifluoromethyl)phenoxy]-1-azetidinecarboxamide and the amount of acetic formic anhydride is doubled:
3-[2-(carboxamido)phenoxy]-1-azetidinecarboxamide,
3-[3-(carboxamido)phenoxy]-1-azetidinecarboxamide, and
3-[4-(carboxamido)phenoxy]-1-azetidinecarboxamide,
there are obtained:
N-formyl-3-[2-(N-formylcarboxamido)phenoxy]-1-azetidinecarboxamide,
N-formyl-3-[3-(N-formylcarboxamido)phenoxy]-1-azetidinecarboxamide, and
N-formyl-3-[4-(N-formylcarboxamido)phenoxy]-1-azetidinecarboxamide.

EXAMPLE 4

N-Hydroxymethyl-3-[3-(trifluoromethyl)phenoxy]-1-azetidinecarboxamide

A mixture of 0.639 g (0.0024 mole) of 3-[3-(trifluoromethyl)phenoxy]-1-azetidinecarboxamide and 6 ml of 37% formaldehyde solution were heated on a water bath at 65° C. for 1 hr, at which time dissolution was complete. The solution was stirred at room temperature for approximately 60 hr. The reaction mixture was divided into two 15 ml centrifuge tubes each extracted three times with ether. The combined extracts were dried over magnesium sulfate, decolorized with charcoal and evaporated to dryness. The residue weighing about 1.5 g was dissolved in ether, washed 5 times with 3 ml of water each time. The ether layer was again dried over magnesium sulfate and evaporated to dryness. The residue was triturated with hexane and ether to give 0.213 g (30.5%) of white powder, m.p. 113°–115° C.

Analysis: Calculated for $C_{12}H_{13}N_2O_3F_3$: C,49.66; H,4.51; N,9.65. Found: C,49.59; H,4.52; N,9.54.

EXAMPLE 5

When in the procedure of Example 4 the following are substituted for 3-[3-(trifluoromethyl)phenoxy]-1-azetidinecarboxamide:
3-(phenoxy)azetidinecarboxamide,
3-[4-(trifluoromethyl)phenoxy]-1-azetidinecarboxamide,
3-[2-(trifluoromethyl)phenoxy]-1-azetidinecarboxamide,
3-[4-(methyl)phenoxy]-1-azetidinecarboxamide,
3-[3,5-(dimethoxy)phenoxy]-1-azetidinecarboxamide,
3-[3-(fluoro)phenoxy]-1-azetidinecarboxamide, and
3-[4-(aceto)phenoxy]-1-azetidinecarboxamide,
there are obtained:
N-hydroxymethyl-3-(phenoxy)azetidinecarboxamide,
N-hydroxymethyl-3-[4-(trifluoromethyl)phenoxy]-1-azetidinecarboxamide,
N-hydroxymethyl-3-[2-(trifluoromethyl)phenoxy]-1-azetidinecarboxamide,
N-hydroxymethyl-3-[4-(methyl)phenoxy]-1-azetidinecarboxamide,
N-hydroxymethyl-3-[3,5-(dimethoxy)phenoxy]-1-azetidinecarboxamide,
N-hydroxymethyl-3-[3-(fluoro)phenoxy]-1-azetidinecarboxamide, and
N-hydroxymethyl-3-[4-(aceto)phenoxy]-1-azetidinecarboxamide.

EXAMPLE 6

When in the procedure of Example 4, the following are substituted for 3-[3-(trifluoromethyl)phenoxy]-1-azetidinecarboxamide and the amount of formaldehyde is doubled:
3-[2-(carboxamido)phenoxy]-1-azetidinecaboxamide,
3-[3-(carboxamido)phenoxy]-1-azetidinecarboxamide, and
3-[4-(carboxamido)phenoxy]-1-azetidinecarboxamide,
there are obtained:
N-hydroxymethyl-3-[2-(N-hydroxymethylcarboxamido)phenoxy]-1-azetidinecarboxamide,
N-hydroxymethyl-3-[3-(N-hydroxymethylcarboxamido)phenoxy]-1-azetidinecarboxamide, and
N-hydroxymethyl-3-[4-(N-hydroxymethylcarboxamido)phenoxy]-1-azetidinecarboxamide.

PHARMACOLOGY: PROCEDURE FOR DETERMINING ANTICONVULSANT ACTIVITY

Anticonvulsant activity of a compound of the invention is determined in mice using Metrazole as the convulsant by the method of Swinyard (see above citation) as follows:

Adult female mice are randomly assigned to dosage groups according to the method of Steel, R. G. D. and Torrie, J. H. (1960) in "Principles and Procedures of Statistics," McGraw-Hill Book Company, Inc., pp. 99–100, pp. 428–31. Each mouse is identified with a color code on its tail. The test compounds are administered as suspensions in 10 ml/kg mouse body weight of 0.5% aqueous methylcellulose within 15 minutes of preparation of the suspension. Metrazole (pentylenetetrazol) is prepared as a solution in physiological saline. The mice are not fasted prior to the test. Eight mice are tested at each level.

Each mouse receives one dose of the test drug in the 0.5% aqueous methylcellulose or the control article (0.5% aqueous methylcellulose alone) intraperitoneally. One-half hour after administration of the test compound, Metrazole (80 mg/kg S.C. in saline) is then given in a loose fold of skin on the back of the neck. Injections are given with a 1-ml glass tuberculin syringe with appropriate size hypodermic needle (27 guage for solutions; 23 guage for suspensions). All injections are given in a volume of 10 ml/kg mouse body weight. Each mouse is observed for 30 minutes following Metrazol injection. Failure of the animals to exhibit a threshold seizure (a single episode of clonic spasms at least 5 seconds in duration) is defined as protection. Anticonvulsant data are calculated in terms of percent protection, i.e., $$\frac{\text{No. mice protected}}{\text{No. mice tested}} \times 100 = \text{percent protected}$$

The $ED_{50}$ and (95% confidence limits) and potency ratio if desired are ascertained by the computer-based probit analysis ascribed to Fenney, D. J. (1964) "Statistical Method in Biological Assay.," 2nd Ed., New York, Hafner Publishing Co.

FORMULATION AND ADMINISTRATION

The pharmacologically active N-formyl and N-hydroxymethyl-3-phenoxy-1-azetidinecarboxamides of this invention are effective in the treatment of both petit mal epilepsy and grand mal epilepsy. Effective quantities of these compounds may be administered to a living animal body orally as in capsules, tablets or elixirs employing the usual pharmaceutical carriers. It is only necessary that the active ingredient constitute an effective amount, i.e., such that a suitable effective dosage will be obtained consistent with the dosage form employed. The exact individual dosage as well as daily dosages will, of course, be determined according to standard medical principles under the direction of a physician or veterinarian.

Based upon a comparison with known anticonvulsant compounds, daily dosages appear to preferably range from about 0.5 to 1.5 milligrams per kilogram of body weight in the treatment of petit mal epolepsy and about 25 to 35 milligrams per kilogram of body weight in the treatment of grand mal epilepsy. Very small quantities of the active materials of the present invention, even as low as 0.1 milligrams, are effective when minor therapy is involved. Unit dosages are usually 5 milligrams or above and preferably 25, 50 or 100 milligrams per unit dosage. The active ingredients of the invention may be combined with other pharmacologically active agents or with buffers, antacids or the like for administration and the proportion of the active agent in the composition may be varied widely.

CAPSULES

Capsules of 5 mg., 25 mg., and 50 mg. of active ingredient per capsule are prepared; with higher amounts of ingredient reduction may be made in the amount of lactose.

| Typical blend for encapsulation | Per Capsule, mg. |
|---|---|
| Active ingredient | 5.0 |
| Lactose | 296.7 |
| Starch | 129.0 |
| Magnesium stearate | 4.3 |
| Total | 435.0 mg. |

Uniformly blend the selected active ingredient with lactose, starch and magnesium stearate and encapsulate the blend.

Additional capsule formulations preferably contain a higher dose of active ingredient and are as follows:

| Ingredients | 100 mg. per Capsule | 250 mg. per Capsule | 500 mg. per Capsule |
|---|---|---|---|
| Active ingredient | 100.0 | 250.0 | 500.0 |
| Lactose | 231.5 | 126.5 | 31.1 |
| Starch | 99.2 | 54.2 | 13.4 |
| Magnesium stearate | 4.3 | 4.3 | 5.5 |
| Total, mg. | 435.0 | 435.0 | 550.0 |

TABLETS

A typical formulation for a tablet containing 5.0 mg. of active ingredient per tablet follows. The formulation may be used for other strengths of active ingredient by adjustment of weight of dicalcium phosphate.

| Ingredients | Per Tablet, mg. |
|---|---|
| (1) Active ingredient | 5.0 |
| (2) Corn Starch | 13.6 |
| (3) Corn Starch (paste) | 3.4 |
| (4) Lactose | 79.2 |
| (5) Dicalcium phosphate | 68.0 |
| (6) Calcium Stearate | 0.9 |
| Total | 170.1 mg. |

Uniformly blend 1, 2, 4 and 5. Prepare 3 as a 10 percent paste in water. Granulate the blend with the starch paste and pass the wet mass through a number eight mesh screen. The wet granulation is dried and passed through a number twelve mesh screen. The dried granules are blended with calcium stearate and compressed.

Additional tablet formulations preferably contain a higher dosage of the active ingredient and are as follows.

| 50 mg. Tablet | |
|---|---|
| Ingredients | Per Tablet, mg. |
| Active ingredient | 50.0 |
| Lactose | 90.0 |
| Milo starch | 20.0 |
| Corn starch | 38.0 |
| Calcium stearate | 2.0 |
| Total | 200.0 |

Uniformly blend the active ingredient, lactose, milo starch and corn starch. The blend is granulated, using water as a granulating medium. The wet granules are passed through an eight mesh screen and dried at 140 to 160 degrees Fahrenheit overnight. The dried granules are passed through a number ten mesh screen and blended with the proper amount of calcium stearate and this blend is then converted into tablets on a suitable tablet press.

What is claimed is:

1. A process which comprises orally administering to a mammal for its anticonvulsant effect an effective amount of a compound selected from the group consisting of N-formyl and N-hydroxymethyl-3-phenoxy-1-azetidinecarboxamides having the formula:

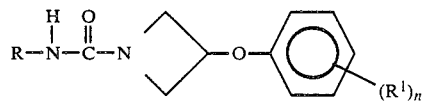

wherein;

R is selected from formyl or hydroxymethyl,

R$^1$ is selected from the group consisting of hydrogen, fluoro, loweralkyl, loweralkoxy, trifluoromethyl, acetyl, N-formylcarboxamido or N-hydroxymethylcarboxamido; and n is selected from 1 to 3 inclusive wherein R$^1$ may be the same or different.

2. The process of claim 1 wherein the compound is N-formyl-3-[3-(trifluoromethyl)phenoxy]-1-azetidinecarboxamide.

3. The process of claim 1 wherein the compound is N-hydroxymethyl-3-[3-(trifluoromethyl)phenoxy]-1-azetidinecarboxamide.

* * * * *

UNITED STATES PATENT AND TRADEMARK OFFICE
CERTIFICATE OF CORRECTION

PATENT NO. : 4,505,907
DATED : Mar. 19, 1985
INVENTOR(S) : George Joseph Wright; Lina Chen Teng It is certified that error appears in the above-identified patent and that said Letters Patent are hereby corrected as shown below:

In the abstract, next to last line, change "anti-depressant" to read --anticonvulsant--

Col. 2, line 23, change "nitrogen" to read --nitrourea--

Signed and Sealed this

Sixth Day of August 1985

[SEAL]

Attest:

DONALD J. QUIGG

Attesting Officer     Acting Commissioner of Patents and Trademarks